United States Patent [19]
Witt

[11] Patent Number: 4,880,988
[45] Date of Patent: Nov. 14, 1989

[54] LIGHT AND WEATHERING TESTING APPARATUS

[75] Inventor: Jürgen Witt, Hainburg, Fed. Rep. of Germany

[73] Assignee: W. C. Heraeus GmbH, Hanau, Fed. Rep. of Germany

[21] Appl. No.: 168,985

[22] Filed: Mar. 16, 1988

[30] Foreign Application Priority Data

Aug. 12, 1987 [DE] Fed. Rep. of Germany ....... 3726803

[51] Int. Cl.$^4$ ............................................. G21K 3/00
[52] U.S. Cl. ................................ 250/504 R; 250/492.1
[58] Field of Search .............. 250/492.1, 493.1, 504 R

[56] References Cited

U.S. PATENT DOCUMENTS

| 3,686,940 | 8/1972 | Kockott | 250/504 R |
| 4,101,424 | 7/1978 | Schooley | 250/504 R |
| 4,644,899 | 2/1987 | Glaus | 250/504 R |
| 4,747,645 | 5/1988 | Rudzki | 250/492.1 |

FOREIGN PATENT DOCUMENTS 2024288 12/1971 Fed. Rep. of Germany .

Primary Examiner—Bruce C. Anderson
Attorney, Agent, or Firm—Frishauf, Holtz, Goodman & Woodward

[57] ABSTRACT

To simplify separation of infrared (IR) radiation from visible and ultraviolet (UV) radiation emitted from a xenon lamp (2), the lamp is surrounded by a cylindrical filter (1) reflecting IR radiation inwardly of the filter but passing UV and visible spectral radiation therethrough. IR radiation reflected inwardly of the filter is absorbed, in accordance with the invention, by an absorbing surface (5) extending axially longitudinally and diametrically across the cylindrical filter, with the cylinder axis (4) of the filter. An auxiliary surface (9) can be positioned between the radiation source and the adjacent nearer side wall of the filter. Reflected IR radiation (8) can thus be absorbed by the IR absorbing surface, with essentially only UV and visible light radiation passing through the cylindrical filter.

19 Claims, 1 Drawing Sheet

LIGHT AND WEATHERING TESTING APPARATUS

Reference to related to patent, assigned to the assignee of the present application, the disclosure of which is hereby incorporated by reference: U.S. Ser. No. 828,830, filed Feb. 12, 1986, RUDZKI 4,747,645, May 31, 1988

Reference to related disclosure: German Pat. No. 20 24 288

The present invention relates to a testing apparatus to test samples for resistance to weathering and light irradiation, and more particularly to such an apparatus which includes a radiation source which emits light in the infrared (IR), visible, and ultraviolet (UV) spectrum of radiation, and in which the sample is exposed to the radiation from the light source.

Background

Weathering and light testing apparatus in which radiation is directed to samples are known, see for example U.S. Pat. No. 4,747,645, based on application Ser. No. 828,830, filed Feb. 12, 1986, Rudzki. A suitable radiation source is a xenon lamp. Such lamps, which either are tubular or have a small, essentially point source radiation element, emit radiation in the visible, UV and IR range. It has previously been proposed to filter IR radiation emitted from the source by placing between the source an the sample a filter which is transparent to the visible and the UV portion of the emitted radiation, but selectively reflects IR radiation. The filter is spaced from the radiation source and, for example, is cylindrical, surrounding the elongated or point-type radiation source. A flat surface can be located within the filter to absorb the radiation.

German Pat. No. 20 24 288 HENSIEK describes a test apparatus to test samples for resistance to light and weather influences. Such apparatus are used to test various materials with respect to aging, by accelerating the impinging radiation, so that a time compressed test can be carried out. To obtain good correlation between natural weathering and radiation effects on the sample, it is necessary to match the spectral energy distribution of the light closely to that of natural sunlight. It is customary to utilize xenon radiators in apparatus of this type. Xenon radiators have a high proportion of radiation in the IR range, and specifically between about 700 to 1000 nm. To obtain a radiation spectrum which matches daylight as closely as possible, it is necessary to substantially reduce IR radiation. This also reduces heating of the sample.

The structure, as proposed, has an external filter in form of a cylindrical jacket, the interior space of which is separated into three regions by mirror surfaces. Each one of the separated regions is associated with an elongated radiation source, extending in axial direction with respect to the filter cylinder. Besides the desired UV and visible light spectrum radiation, a substantial proportion of IR radiation is emitted by the light source. The mirror surfaces are transparent for IR radiation, but reflect UV radiation at the surface. The cylindrical jacket is transparent for UV and visible radiation, reflecting, however, IR radiation into the interior of the cylinder. The IR radiation passing through the mirror surfaces is absorbed within the structure. Heat, which results, is removed from the absorption space.

The Invention

It is an object to simplify a structure which provides, essentially only UV and visible spectral radiation, which is efficient, and in spite of simplicity of construction permits absorption of a substantial portion of IR radiation emitted from the radiation source without, however, reducing UV and visible radiation emitted to the outside of the apparatus.

Briefly, the radiation source which may be a lamp having essentially point or small area light emitting characteristics, or may be an elongated tubular lamp, is located within a cylindrical filter defining a central axis, which filter is transparent to UV and visible radiation but reflects IR radiation internally. The radiation source is located eccentrically with respect to the cylinder axis of the filter cylinder, and positioned in a plane which includes the axis of the cylinder and the radiation source, the plane also retaining a radiation absorbing element defining a plane surface. The radiation absorbing element extends from an inside wall of the cylindrical filter up to the radiation source; another portion of the radiation absorbing element may extend from the light source towards the opposite side of the inside wall of the cylinder, in line with the major portion of the radiation absorbing element extending part-diametrically across the cylindrical filter.

The arrangement has the advantage of utmost simplicity while being highly efficient. The radiation source is in the plane of at least one IR radiation absorbing surface. The radiation source, thus, is not in the axis of the hollow cylindrical filter so that the entire IR radiation which is emitted from the radiation source can be reflected by the cylindrical filter internally of the cylindrical structure and to the IR radiation absorbing surface. The heat generated, thereby, can be conducted away from the IR radiation absorbing surface. On the other hand, UV radiation and visible light radiation can pass through the essentially cylindrical filter without any impediment towards the outside, and, for example, against the test sample.

The construction is very simple and inexpensive, since no expensive filter and mirror surfaces are needed. The region between the cylindrical jacket and the radiation source, namely that region plane which is opposite and coplanar to the zone of the radiation absorbing surface which extends towards the radiation source, is practically free from radiation with respect to reflected IR radiation from the inner surface of the cylinder of the filter.

A further surface can be located within the cylindrical filter of the apparatus which is located in the plane of the main radiation absorbing surface and extends from the source, in the back of the main surface of the inner wall of the cylindrical filter. This arrangement provides for subdivision of the interior space of the filter into two halves of essentially the same size. Preferably, the radiation source is so located within the inside of the filter that it is spaces from the inner surface of the cylinder by a distance which corresponds to approximately one-quarter of the interior diameter of the filter. The axis of the radiation source should be offset from the axis of the cylindrical filter by preferably at least one half the outer diameter of the bulb of the radiation source; in other words, no portion of the radiation' source should intersect the axis of the cylinder, or be tangent to the axis of the cylinder. Dimensioning the apparatus in such a manner obtains reflection of all of the IR radiation from the inner wall of the filter on to the radiation absorbing surface.

In accordance with a preferred feature of the invention, the radiation source is an elongated tubular element, having an axis parallel to the axis of tubular filter. This provides for uniform intensity of radiation over the entire longitudinal extent of the tubular filter. It is also possible, however, to use an essentially punctiform radiation source; if so, it is preferably located essentially in the center of the filter, that is, at half the axial length of the cylinder.

The filter itself is a cylinder which is coated at the inside or at the outside with a material which, preferably, is a dialectric, and is characterized by good reflectivity within the IR spectral range while having high transparency for radiation in the UV and visible range.

DRAWINGS, SHOWING AN ILLUSTRATIVE EXAMPLE

FIG. 1 is a perspective view of a radiation source in accordance with the present invention; and FIG. 2 is a cross-sectional view through FIG. 1, and also illustrating, highly schematically, a test sample.

Detailed Description

Figure 1:
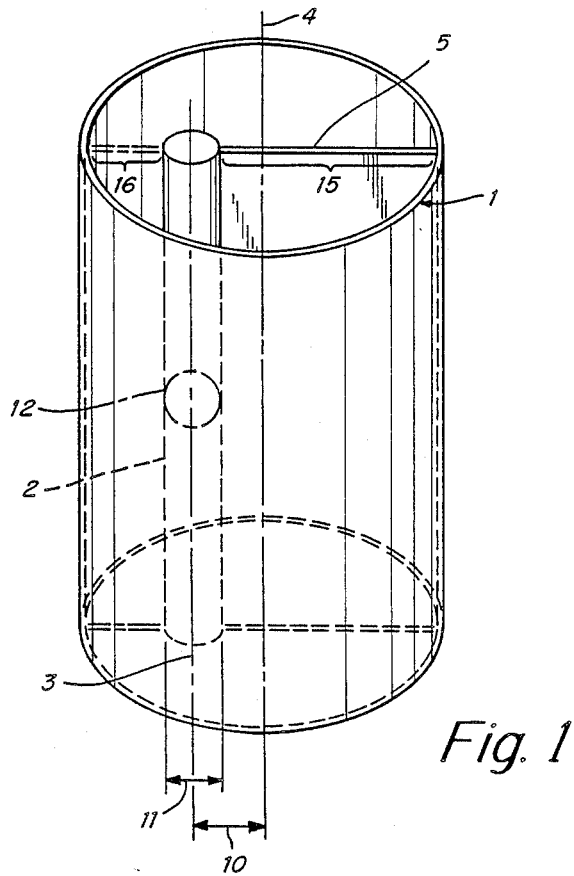
Figure 2:
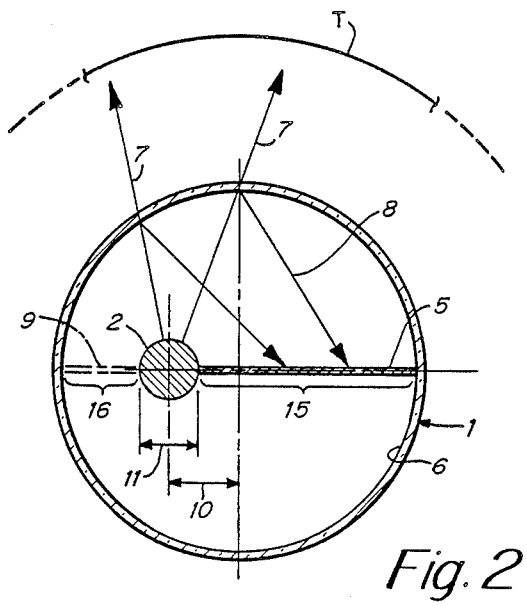

The radiation arrangement is used in a test apparatus to test permanence of a test sample T (FIG. 2) with respect to influences of light and weather. A tubular cylindrical filter 1 surrounds a radiation source 2. The radiation source, preferably is an elongated tubular source having a longitudinal axis 3 which is arranged parallel to the axis 4 of the cylindrical filter 1. The radiation source is spaced from the axis 4 of the filter 1. The axis 3 of the radiation source 2 and the axis 4 of the filter 1 together define a plane in which an IR radiation accepting element defining a flat surface 5 is located. The surface element 5 subdivides, in the region 15 between radiation source 2 and the inner surface of the filter 1, the interior space of the tubular filter 1. The region 16 between the light source 2 and the other or diametrically opposite wall portion of the filter 1 can be closed off by another IR absorbing element 9 (FIG. 2) or can be left open (FIG. 1) as desired. Looked at in cross section, as seen in FIG. 2, the surface 5 is placed in the region which has the largest spacing between the radiation source and the inner surface of the filter 1, and defined by the axis 4 of the filter and the axis 3 of the radiation source. The inner surface of the filter is coated with a filter layer 6 of a dialectric material which has the characteristic that the radiation from the radiator 2 is selectively divided. The filter layer 6 is transparent for UV radiation and for visible radiation, as schematically shown by arrows 7. The layer 6 is, however, reflective for IR radiation, as schematically shown by arrows 8, which IR radiation is reflected back into the interior space of the filter 1. The reflected IR radiation impinges on the absorbing surface 5. A suitable element forming the surface 5 is a flat sheet-metal structure which is blackened. Radiation accepted by the element defining the surface 5 can thus be readily carried away as heat. It is possible to construct the element defining the surface 5 as a cooled structure, if desired. In order to further suppress IR radiation randomly reflected in the inside of the tube 1, a further absorbent surface 9, similar to surface 5, can be placed in the region 16 (FIG. 2), and co-planar with the surface 5. Preferably, the radiation source 2 is so located that its axis 3 has a distance 10 from the axis 4 of the filter 1 which is about 1.5 times the diameter 11 of the radiator source 2. Preferably the radiation source is a xenon radiator. Further the center of the axis 3 of the radiation 2 is offset at the most by 0.25 of the inner diameter of the filter 1 from the axis 4 of the filter 1. By locating the radiation source 2 eccentrically with respect to the axis 4 of the cylindrical filter 1, the entire reflected IR radiation, reflected from the inner surface of the filter 1, is directed to the absorbing surface 5 and, possibly, any stray radiation to the surface 9, if used.

A source 2 may be used which, rather than being cylindrical, is essentially spherical or bulbous in shape. Such a source is schematically shown by the circle 12 (FIG. 1). Since the radiation source, as such, is well known and a standard article of commerce, it need not be further described and any suitable such source may be used. Is an essentially punctiform or bulbeous radiation source if used, it is preferably located at about half the axial height of the cylinder 1.

Various changes and modification may be made within the scope of the invention concept.

A suitable material for the dielectric IR reflective UV and visible transmissive coating 6 is a compound comprising $SiO_2$, $ThO_2$, $Al_2O_3$, $Fe_2O_3$; the material for the tubular cylindrical support is $SiO_2$.

I claim:

1. Light and weathering testing apparatus having
   a radiation source (2) for irradiating a test sample (T), said source emitting light in the ultraviolet (UV), visible and infrared (IR) spectral ranges;
   a cylindrical filter (1) defining a cylinder axis (4), surrounding the source (2) and spaced therefrom, said filter (1) being transparent for UV and visible radiation, and reflecting IR radiation; and
   IR radiation absorbent means (5) for absorbing said IR radiation reflected from said filter; further comprising, in accordance with the invention,
   means for directing substantially all of said reflected IR radiation onto absorbent means (5, 9) located along a single plane, namely a spatial arrangement in which said radiation source is located eccentrically with respect to the cylinder axis (4) of the filter (1), but in a plane which includes the filter cylinder axis (4), said radiation source (2, 3) and said filter cylinder axis (4) thereby defining a reflected-radiation-receiving plane; and
   wherein the IR radiation absorbent means (5) extends along said reflected-radiation-receiving plane from an inside wall of the cylindrical filter (1) up to the radiation source (2) part-diametrically across the cylindrical filter (1).

2. The apparatus of claim 1, wherein a further absorbent surface (9) is provided, co-planar with said absorbent surface (5) and extending from the radiation source (2) to an adjacent inner surface of the filter.

3. The apparatus of claim 1, wherein the radiation source (2) defines a central point;
   and wherein said central point is spaced from said cylinder axis (4) of the filter by a distance (10) which comprises at least half the external diameter (11) of the radiation source (2)

4. The apparatus of claim 3, wherein the radiation source (2) defines a center;
   and wherein said center is eccentrically positioned from said cylinder axis (4) of the filter by a distance which is at most one-quarter of the inner diameter of the cylindrical filter (1).

5. The apparatus of claim 4, wherein a further absorbent surface (9) is provided, co-planar with said absorbent surface (5) and extending from the radiation source (2) to an adjacent inner surface of the filter.

6. The apparatus of claim 5, wherein said light source (2) is a xenon lamp.

7. The apparatus of claim 5, wherein said light source (2) is an elongated xenon lamp defining an axis (3) extending essentially parallel to the cylinder axis (4) of the tubular filter (1).

8. The apparatus of claim 5, wherein said light source (2) is an essentially point-like or bulbous xenon lamp.

9. The apparatus of claim 1, wherein the radiation source (2) defines a center;
and wherein said center is eccentrically positioned from said cylinder axis (4) of the filter by a distance which is at most one-quarter of the inner diameter of the cylindrical filter (1).

10. The apparatus of claim 1, wherein the tubular filter (1) comprises a transparent support and a filter layer (6) including dialectric material.

11. The apparatus of claim 1, wherein said source (2) comprises an elongated light source (2) defining a central axis (3).

12. The apparatus of claim 1, wherein said light source comprises an elongated tubular radiation source (2) defining a central axis (3) which extends parallel to the cylinder axis (4) of the filter (1).

13. The apparatus of claim 1, wherein said light source comprises an essentially point light source (12).

14. The apparatus of claim 1, wherein said light source (2) is a xenon lamp.

15. The apparatus of claim 14, wherein a further absorbent surface (9) is provided, co-planar with said absorbent surface (5) and extending from the radiation source (2) to an adjacent inner surface of the filter.

16. The apparatus of claim 1, wherein said light source (2) is an elongated xenon lamp defining an axis (3) extending essentially parallel to the cylinder axis (4) of the tubular filter (1).

17. The apparatus of claim 16, wherein a further absorbent surface (9) is provided, co-planar with said absorbent surface (5) and extending from the radiation source (2) to an adjacent inner surface of the filter.

18. The apparatus of claim 1, wherein said light source (2) is an essentially point-like or bulbous xenon lamp.

19. The apparatus of claim 18, wherein a further absorbent surface (9) is provided, co-planar with said absorbent surface (5) and extending from the radiation source (2) to an adjacent inner surface of the filter.

* * * * *